United States Patent [19]

Martin et al.

[11] Patent Number: 5,100,320
[45] Date of Patent: Mar. 31, 1992

[54] DENTAL PACKAGING MATERIAL AND CARTRIDGE

[75] Inventors: Thomas W. Martin; Jeffrey S. Steinmetz, both of St. Paul; Scott R. Culler, Burnsville, all of Minn.

[73] Assignee: Minnesota Mining and Manufacturing Company, St. Paul, Minn.

[21] Appl. No.: 465,802

[22] Filed: Jan. 16, 1990

[51] Int. Cl.$^5$ ............................................. A61C 5/04
[52] U.S. Cl. .............................................. 433/90
[58] Field of Search ............. 433/90; 206/63.5, 524.4, 206/524.5, 524.6

[56] References Cited

U.S. PATENT DOCUMENTS

| | | | |
|---|---|---|---|
| 2,903,794 | 9/1959 | Carfagni | 433/90 |
| 3,581,399 | 6/1971 | Dragan | 32/60 |
| 3,595,439 | 7/1971 | Newby et al. | 222/80 |
| 3,900,954 | 8/1975 | Dragan | 32/60 |
| 4,084,320 | 4/1978 | Skeirik | 433/90 |
| 4,391,590 | 7/1983 | Dougherty | 433/90 |
| 4,551,135 | 11/1985 | Gorman et al. | 433/90 X |
| 4,552,266 | 11/1985 | Weissenburger | 206/63.5 X |
| 4,664,257 | 5/1987 | Wilson | 206/63.5 X |
| 4,767,326 | 8/1988 | Bennett et al. | 433/90 |
| 4,798,596 | 1/1989 | Mühlbauer | 433/90 X |

FOREIGN PATENT DOCUMENTS

| | | | |
|---|---|---|---|
| 2260515 | 9/1975 | France | 433/90 |
| 0151036 | 11/1981 | Japan | 206/63.5 |

*Primary Examiner*—John J. Wilson
*Assistant Examiner*—Todd E. Manahan
*Attorney, Agent, or Firm*—Gary L. Griswold; Walter N. Kirn; Douglas E. Reedich

[57] ABSTRACT

A cartridge made of a material that does not to a significant extend absorb polar components from a dental composition stored therein. The force required to extrude a dental composition from the cartridge increases less over time in a cartridge of the invention than in a cartridge of the same configuration made of conventionally employed materials such as nylon-6.

22 Claims, 1 Drawing Sheet

DENTAL PACKAGING MATERIAL AND CARTRIDGE

BACKGROUND OF THE INVENTION

1. Technical Field

This invention relates to packaging dental products such as adhesives, composites, cements, etching gels, restoratives, sealants, and the like. In another aspect, this invention relates to cartridges for storage and delivery of such dental products. This invention also relates to packaged, premeasured dosage forms of such dental products.

2. Description of the Related Art

Cartridges for the storage and delivery of predetermined amounts of a dental material are known and described, for example, in U.S. Pat. Nos. 3,581,399, (Dragan) 3,595,439 (Newby et al.), 3,900,954 (Dragan), 4,391,590 (Dougherty), and 4,767,326 (Bennett et al.).

The cartridges described in Newby et al. are said to be made of polypropylene, polystyrene, or preferably polyethylene. The cartridges described in the other above-listed patents are said to be made of plastic materials without further description of the particular plastic used. Most current products, for example Prisma TM APH dental restorative material (L. D. Caulk) and Herculite TM XR dental restorative material (Kerr), are sold in cartridges made of nylon-6.

SUMMARY OF THE INVENTION

Many dental restorative compositions become more viscous upon storage in the nylon-6 cartridges in which they are sold. We feel that this is caused by a previously unrecognized absorption of polar components from the composition into the cartridge itself. Accordingly, some of the desired physical handling and dispensing properties of the compositions are compromised. Further, upon storage, the force required to extrude a composition from a nylon-6 cartridge can become so high that the cartridge bursts when the composition is extruded at a useful rate, particularly when a relatively viscous dental composition is extruded.

This invention overcomes this problem by providing a cartridge specially adapted to be mounted in a hand-held ejector-type gun, comprising:

a hollow cartridge body having an inner wall defining an elongate inner chamber open at one end of the body and adapted at the open end to be detachably mounted in the gun, and having at the opposite end of the body an orifice to allow discharge of a dental composition from the inner chamber; and a piston inserted into the open end of the body, wherein the body has a burst strength greater than that of an otherwise identical body made entirely of polypropylene, and the inner wall material has a 24 hour water absorption less than that of nylon-6.

Another embodiment of this invention provides a cartridge of the configuration described above and which has an extrusion force less than the extrusion force exhibited by an otherwise identical nylon-6 cartridge when both are filled with a dental composition and aged two weeks according to the Extrusion Force Test described in detail below, and wherein the body has a burst strength greater than that of an otherwise identical body made entirely of polypropylene.

This invention also provides cartridges as described above wherein the inner chamber contains a dental restorative composition comprising a polar monomer.

DESCRIPTION OF THE DRAWING

This invention is better understood by reference to the Drawing, wherein.

DETAILED DESCRIPTION OF THE INVENTION

Figure 1:
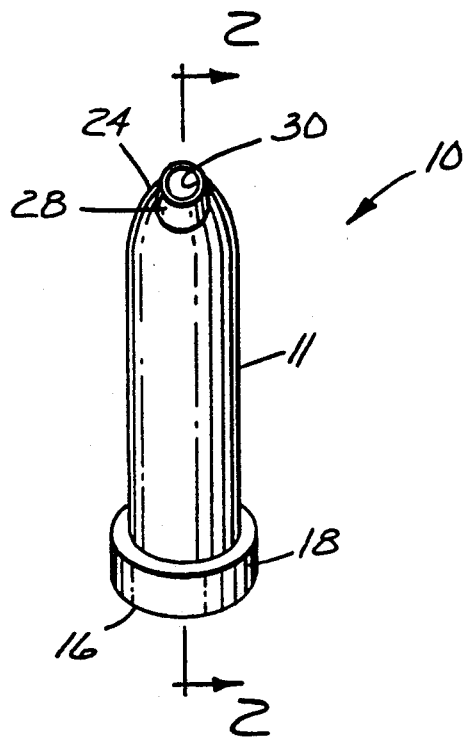
FIG. 1 is a perspective view of a cartridge of the invention, filled with a dental restorative composition.

The cartridges of the invention have an inner wall that does not to a significant extent absorb polar components from a dental composition. A dental composition stored in a cartridge of the invention maintains desirable properties for an extended period of time compared to the same composition stored in a cartridge made of the currently commercially preferred material, nylon-6.

The body of a cartridge of the invention is preferably made entirely of a material that does not absorb polar components from a dental composition. In such a cartridge, the inner wall will necessarily be made of such material. The piston, too, is preferably made of a material that does not absorb polar components, and it is most preferably made of the same material from which the body is made. Other suitable constructions of a cartridge of the invention include those wherein an appropriate inner wall is created by the presence of a sleeve or a lining made of a material that does not absorb polar components within a cartridge body otherwise made of a material that does absorb polar components (e.g., nylon-6). Also, constructions are suitable wherein a cartridge body is made of a material that does absorb polar components, if the inner wall is rendered suitably non-absorbent by an appropriate surface treatment (e.g., treatment with a protective chemical such as a fluorochemical).

While the tendency of an inner wall material to absorb polar components from a dental composition is not conveniently measured, it is adequately approximated by the tendency of the material to absorb water when immersed in water and tested for 24 hour water absorption according to ASTM D570. In instances where the inner wall material is a chemically or physically treated material, the test is conducted on a sample of the material the entire exterior of which has been subjected to substantially the same treatment.

The particular preferred 24 hour water absorption value will depend to a degree on factors such as the nature of the dental composition contained in a cartridge of the invention (e.g., viscosity, and the relative amounts of water or other polar components to other non-absorbed components) and the dimensions of a cartridge of the invention (e.g., the ratio of the internal volume of the cartridge to the surface area of the inner wall, which relates to the relative amount of the dental composition in a cartridge that will be affected by the internal surface of the cartridge). It is therefore not practical to enumerate a particular 24 hour water absorption limit suitable for use with any and all dental compositions. In general, however, the inner wall material of a cartridge preferably has a 24 hour water absorption of less than about 1 percent, more preferably less than or equal to about 0.5 percent, and most preferably less than or equal to about 0.3 percent when tested according to ASTM D570.

The effectiveness of an inner wall with low water absorption in minimizing or preventing an increase in the viscosity of a dental composition due to absorption of polar components from the dental composition into the cartridge during storage is reflected in the force required to extrude the dental composition from a cartridge of the invention (i.e., the extrusion force) after storage of a filled cartridge for a period of time. Extrusion force increases less over time in a cartridge of the invention than in an otherwise identical cartridge made of nylon-6. In a preferred embodiment of the invention, a cartridge has an extrusion force less than about 80 percent, preferably less than about 60 percent, of the extrusion force of an otherwise identical nylon-6 cartridge when both are filled with a dental composition and aged two weeks according to the Extrusion Force Test described in detail below. The various forms of nylon-6 have 24 hour water absorption values in the range from 1.0 to 11 percent. The particular nylon-6 used in the above-discussed comparison should be the least water-absorbant nylon-6 from which current commercial cartridges are made. A cartridge that bursts when the Extrusion Force Test is applied is of course not suitable to use in the Test and is not a preferred embodiment of the invention. Such a cartridge, however, might still be useful for low viscosity dental compositions and thus within the ambit of the invention.

It is preferred that a cartridge have sufficient strength to withstand the pressures exerted during the extrusion of relatively viscous dental compositions. Tensile strength of the material from which the body of a cartridge is made gives some indication of the strength of the resulting cartridge. Accordingly, it is preferred that the body of a cartridge of the invention be made of a material with a tensile strength greater than that of polypropylene, perferably at least about 40,000 kPa, more preferably at least about 56,000 kPa, and most preferably at least about 84,000 kPa.

Factors other than tensile strength of the material can affect the structural integrity of the cartridge. For example, the particular configuration of the cartridge can cause inherent structural weakness. Further, in an injection-molded cartridge, less than optimal mold gating can cause the formation of weak weld lines in the resultant cartridge. Also, the material can become oriented such that a cartridge will be strong along one axis and weak along another.

A cartridge therefore might be susceptible to bursting during use even if it is made of a material with high tensile strength. It is possible, however, to directly measure the strength of a cartridge of the invention by employing the Burst Strength Test described in detail below. A cartridge of the invention preferably exhibits a burst strength of at least about 25 kg, more preferably at least about 40 kg, and most preferably at least about 50 kg.

Preferred materials for use in the construction of a cartridge of the invention are those that are inert to the dental composition to be placed therein, suitably nontoxic for use in the mouth, having a 24 hour water absorption lower than that of nylon-6 and capable of providing a cartridge that has a burst strength greater than that of an otherwise identical cartridge made entirely of polypropylene. Further, in the case of a cartridge that is to be used with a photocurable dental composition, it is preferred that the cartridge be opaque to light capable of curing the dental composition.

Preferred materials include polymeric materials with tensile strength higher than that of polypropylene or with other properties that will provide a cartridge with a burst strength greater than that of an otherwise identical cartridge made entirely of polypropylene, and with a 24 hour water absorption less than that of nylon-6. Suitable polymeric materials can be selected by those skilled in the art and include some polyamides such as nylon-11, nylon-12, nylon-6,9, and nylon-6,12; and mixtures and blends thereof.

A polymeric material from which a cartridge of the invention is made can also comprise a reinforcing filler. Suitable reinforcing fillers include carbon fiber, mica, calcium carbonate, talc, polytetrafluoroethylene, glass (e.g., chopped glass, continuous glass fiber), aluminum flake, mixtures thereof, and the like.

Polymeric materials with low water absorption but with unsuitable tensile strength such as polyolefins (polyethylene, polypropylene, polyisobutylene), polystyrenes, fluorocarbon and fluoroalkoxy resins (e.g., Teflon TM FEP, Teflon TM PFA, Tefzel TM, DuPont), fluoroethylene-propylene copolymers, and others known to those skilled in the art, can be rendered suitably strong by the use of such reinforcing fillers. The particular amount of a reinforcing filler that can be used with a material varies from filler to filler and from material to material. Therefore it is impractical to recite a particular range of filler levels suitable to all fillers and all polymeric materials. In general, however, a filled material can comprise about 10 percent to about 60 percent, preferably 20 percent to about 50 percent, by weight reinforcing filler based on the total weight of the filled material.

The addition of a reinforcing filler generally lowers the 24 hour water absorption of a polymeric material. Therefore, polymeric materials with relatively high 24 hour water absorption can be used in the construction of a cartridge of this invention if a suitable amount of a reinforcing filler is added such that the resultant 24 hour water absorption is sufficiently low. Examples of such materials include some polyamides such as some forms of nylon-6 (those with lower 24 hour water absorption are preferred) and nylon-6 ,6; polyesters (e.g., polyethylene terephthalate, polybutylene terephthalate); polycarbonates (e.g., Lexan TM from General Electric, Macrolan TM from Mobay, Calibre TM from Dow); and mixtures and blends thereof. Suitable reinforcing fillers and suitable amounts thereof are discussed above in connection with polymeric materials having low 24 hour water absorption.

Some of the above-listed materials are suitably opaque for use with a photocurable dental compositions. Transparent materials can be made opaque by coating (e.g., painting or covering with a label) or preferably by incorporating pigments such as titanium dioxide and carbon black, or colorants (e.g., pigments and/or dyes) in order to prevent light from reaching the dental composition contained therein. Colorants can be incorporated into the material according to well known methods, e.g., as disclosed in the *Modern Plastics Encyclopedia*, Vol. 65, No. 11, pp. 148–150, McGraw-Hill, New York (1988). The particular colorant necessary to absorb light of a selected wavelength can be readily determined by those skilled in the art. Various commercially available colorants known by their color index identification (See *Colour Index Third Edition*, The Society of Dyers and Colourists, England, 1971) absorb different wavelengths of light. The material preferably transmits only light outside the range of wavelengths that will cure the light-curable composition contained therein.

Figure 2:
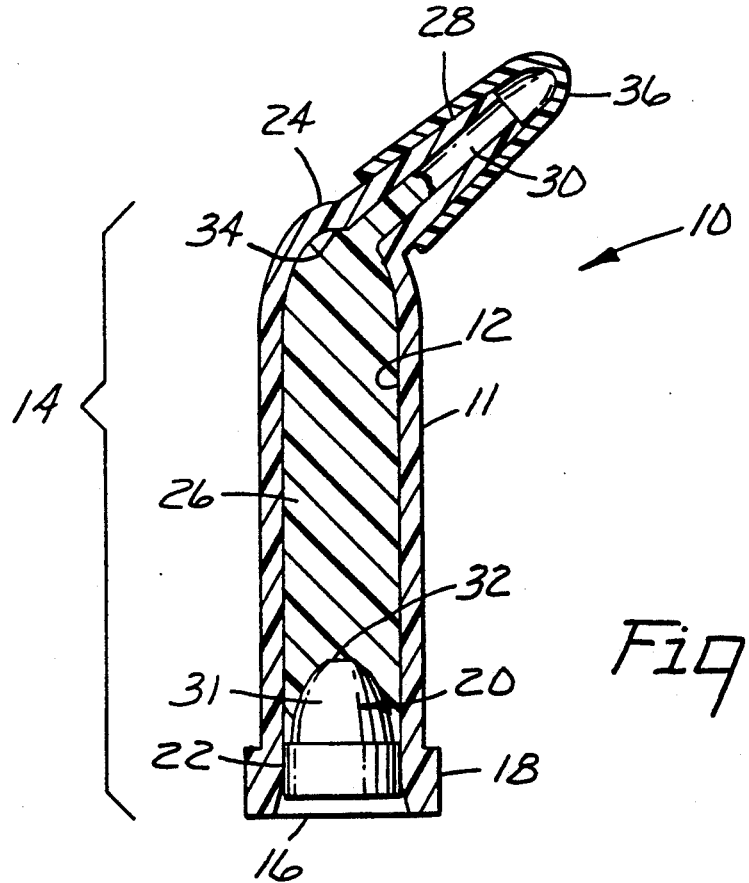
FIG. 2 is a sectional view of the embodiment of FIG. 1 along line 2—2, but including a cap over the discharge nipple.

A cartridge of the invention is preferably adapted to be operated by mounting in a hand-held ejector-type gun such as those described in U.S. Pat. Nos. 4,198,756, 4,391,590, and 4,472,141, the disclosures of which are incorporated herein by reference. Cartridge shapes that can be used in the invention include those described in above-cited U.S. Pat. No. 4,391,590, and U.S. Pat. No. 4,767,326 (the disclosure of which is incorporated herein by reference). Referring to the Drawing, FIGS. 1 and 2 illustrate embodiment 10 of a cartridge of the invention. Referring to FIG. 2, the illustrated embodiment 10 comprises generally cylindrical body 11 with generally cylindrical inner wall 12 defining elongate inner chamber 14. The body has open end 16 adapted by way of annular flange 18 to be detachably mounted in a hand-held ejector-type gun (not shown).

Displaceable piston 20 is inserted in open end 16. Sidewall 22 of piston 20 is in the form of a flange about the circumference of piston 20 and is in sealing conformance with inner wall 12. Piston 20 serves to seal the open end of the cartridge during storage in order to prevent exposure of enclosed dental composition 26 to air. Piston 20 can be displaced toward discharge end 24 of body 10 by means such as a conventional handheld, manually powered, air powered, or motor powered ejector-type gun. When piston 20 is displaced toward discharge end 24, dental composition 26 is expressed from discharge nipple 28, which extends from discharge end 24 and has orifice 30 through which the dental composition is discharged. Piston 20 has bullet-shaped head 31 with a flattened end 32. The discharge orifice can be sealed with removable cap 36, which serves to seal the discharge end of the cartridge during storage.

A cartridge of the invention is preferably relatively small, and is intended to contain an amount of a dental composition that can be substantially fully expended during the course of a single procedure or several (e.g., 2 to about 10) procedures. The volume of the inner chamber (as measured by the volume displaced by the piston's travel) is therefore preferably from about 0.1 mL to about 3 mL, more preferably from about 0.3 mL to about 1 mL. The cross-sectional area of the inner chamber in the plane normal to the longitudinal axis of the inner chamber is relatively small, preferably less than or equal to about 50 mm$^2$, more preferably less than or equal to about 40 mm$^2$ and most preferably less than or equal to about 20 mm$^2$. Cartridges of such dimension benefit more fully from the use of materials with low 24 hour water absorption in their construction, compared to cartridges such as conventional multi-dose syringes with large dimensions where the effect of the inner wall of the cartridge on the dental composition is less significant.

Wall thickness is such that the cartridge will withstand the pressures exerted during extrusion of a dental composition at a useful rate without bursting or excessive yielding. Preferred wall thickness will vary based on several factors, such as the viscosity of the dental composition, the tensile strength of the material from which a cartridge is made, the dimensions of the inner chamber (e.g., length, shape, and cross-sectional area), and the size of the orifice in the discharge nipple. As the cartridge is intended primarily for use in dispensing small amounts of a dental composition to a particular area of the mouth, it is preferred that the orifice in the discharge end be relatively small so as to deliver a controlled amount of dental composition that can be placed with precision. Accordingly, the orifice preferably has a cross-sectional area of less than or equal to about 2 mm$^2$, more preferably less than or equal to about 1 mm$^2$. Particular dimensions for various embodiments will be easily determined by those skilled in the art. For the particular embodiment illustrated in the Drawing, the inside diameter of inner chamber 14 is preferably from about 2 mm to about 7 mm, more preferably from about 3 mm to about 5 mm. The length of body 10 is preferably from about 2 cm to about 8 cm, more preferably from about 2 cm to about 4 cm. The discharge nipple can be of any suitable length, e.g., 1 cm, and the circular orifice in the discharge nipple is preferably about 1 mm in diameter.

While the embodiment illustrated in the Drawing represents a preferred configuration of a cartridge of this invention, those skilled in the art will recognize that the particular configuration of the cartridge is not unduly critical to this invention. Other configurations are suitable. For example, while it is preferred that the discharge nipple be integral with the body of the cartridge, embodiments wherein the discharge end of the cartridge is adapted in the manner of a Luer-lok TM tip, a friction fit tip, a bayonet type fitting, or a screw-on tip are suitable. Further, while it is preferred to seal the discharge nipple with a removable cap, a tip closed by ultrasonic bonding or spin welding and intended to be opened by mechanical means (e.g., cutting), or the like, is suitable as well. Likewise, while it is preferred that the discharge orifice open into a discharge nipple that is angularly disposed to the longitudinal axis of the body, embodiments wherein the discharge nipple is not angularly disposed are suitable as well. Also, the illustrated piston configuration is preferred because the portion of the dental composition that has been in the vicinity of the piston throughout the period of storage (and therefore is more susceptible to the adverse effects of any absorption into or passage through the piston, and leakage at the piston/inner wall junction) is not extruded from the cartridge. It also offers less potential for the degradation of a dental composition by shear forces during extrusion. However, embodiments wherein the piston head is closely complementary to the inner surface of the discharge end are suitable. The inner wall can define an inner chamber of any suitable cross-sectional shape in the plane normal to its longitudinal axis (e.g., a circle, ellipse, polygon, or the like), and the open end can be adapted in any suitable manner to be detachably mounted in a hand-held ejector-type gun.

A cartridge of the invention is preferably made by injection molding.

A cartridge of the invention can be used to advantage with any dental composition that comprises a polar monomer and requires controlled viscosity. Such dental compositions include restoratives, cements (e.g., luting cements, orthodontic cements), etching gels, adhesives, glass ionomer cements, sealants, and the like. Particularly preferred dental compositions include light-curable non-toxic pastes that preferably contain a photoinitiator and a dental filler dispersed in a resin. Resins useful in such a dental composition are hardenable organic compounds having sufficient strength, hydrolytic stability, and non-toxicity to render them suitable for use in the mouth. Examples of such resins include acrylate, methacrylate, urethane, and epoxy resins. Mixtures and derivatives of such resins are also useful. Preferably, the resin is a mixture of diglycidylmethacrylate of Bisphenol A ("Bis-GMA") and triethyleneglycol dimethacrylate ("TEGDMA"). Other details of such compositions will be readily apparent to those skilled in the art.

STRENGTH TEST

The discharge end of a cartridge is plugged in any appropriate manner such that the plug remains in place during the test. In the EXAMPLES below, a small amount of Silux TM Plus light cure dental restorative material (3M) was placed in the open end of the cartridge and cured with a Visilux TM 2 dental curing light (3M) for about 20 seconds and then allowed to drop into the inner chamber of the cartridge.

About one-half of the inner chamber is then filled with uncured "Silux Plus" restorative. The piston is placed in the open end of the body. The cartridge is then placed in an Instron TM Model 1123 tensile testing machine operated at a crosshead speed of 100 mm/min. The piston is displaced by the tensile testing machine toward the discharge end until the cartridge fails by bursting. The force required to cause such failure is measured, and the average of five independent determinations is recorded.

EXTRUSION FORCE TEST

Twenty cartridges of the invention are approximately two-thirds filled with "Silux Plus" restorative. A piston is placed in the open end of each cartridge. Five cartridges are immediately tested for extrusion force as follows: Each filled cartridge is placed in an "Instron" Model 1123 tensile testing machine and the restorative is extruded from the discharge end of the cartridge at a crosshead speed of 100 mm/min. The force required to extrude the restorative is measured, and the average of five independent determinations is recorded. In actual practice, the force required to extrude the restorative is not constant throughout the process of extrusion. Rather, during extrusion the force increases to a plateau, and then the force remains relatively constant for the remainder of the extrusion process. For the purposes of the instant specification and claims, the extrusion force is taken to be the average force observed from the time at which the plateau is reached until the end of the extrusion process.

The remaining fifteen cartridges are sealed by capping the discharge nipple and placed in an oven at 45° C. and ambient humidity. At various time intervals, the aged cartridges are removed from the oven and stored at room temperature and ambient humidity for about 4 hours. The cap is removed from the discharge nipple, the cartridge is placed in the tensile testing machine, and the extrusion force is measured as above.

Cartridges like the cartridges of the invention but made of nylon-6 with a 24 hour water absorption of 1.2 percent are tested as described above and the results are compared to those obtained with the cartridges of the invention.

The examples below are intended to illustrate the invention. They are not intended to limit the invention. All parts and percentages are by weight unless otherwise indicated.

EXAMPLES

Various commercially available dental composite materials were tested according to the EXTRUSION FORCE TEST set forth above. Herculite TM XR restorative (Kerr, a division of Sybron, Inc.) and Prisma TM APH restorative (L. D. Caulk, a division of Dentsply International, Inc.) were obtained in preloaded cartridges made of nylon-6. (The particular 24 hour water absorption of the nylon-6 used in these cartridges is not known to us. However, the lowest value of 24 hour water absorption for a commercial nylon-6 known to us is 1.0 percent.) These compositions were also obtained in larger multi-dose syringes, removed from the syringes, and independently loaded into cartridges made from 20 percent glass fiber reinforced polypropylene (GFRP). The cartridge bodies used in the EXAMPLES and in Comparative Example A were of the general configuration illustrated in the Drawing, with an inside diameter of 4.06 mm, wall thickness of 1.21 mm, a body length of 23.3 mm, a 1.07 mm orifice in the discharge end, and a discharge nipple about 9 mm long. The cartridges used in Comparative Examples B and C were the indicated commercially available preloaded cartridges.

"Silux Plus" restorative was loaded into cartridges made of nylon-6 with a 24 hour water absorption of 1.2 percent. This nylon-6 was chosen because it is at the lower end of the range of 24 hour water absorption values for commercially available forms of nylon-6. However, we do not know if this nylon-6 has a lower 24 hour water absorption value than that used in the commercially available preloaded cartridges of Comparative Examples B and C. "Silux Plus" restorative was also loaded into GFRP cartridges and into cartridges of the same configuration made of 50 percent glass fiber reinforced nylon-6,12 (GFRN).

The filled cartridges were tested immediately for extrusion force as described in the EXTRUSION FORCE TEST above, aged for the specified period of time, and again tested as described in the EXTRUSION FORCE TEST.

For each of Comparative Examples (A), (B), and (C) involving a nylon-6 cartridge, and for each of EXAMPLES 1-4 involving a cartridge of the invention, the TABLE lists cartridge material, dental composition contained therein, aging time, 24 hour water absorption of the cartridge material as determined by ASTM D570, and Burst Strength of the cartridge as determined by the BURST STRENGTH TEST.

TABLE

| Example or Comparative Example | Cartridge Material | Dental Composition | Aging Time (Days) | Extrusion Force (Kg) | Burst Strength (Kg) | 24 Hour Water Absorption (percent)[4] |
|---|---|---|---|---|---|---|
| Comparative Example A | nylon-6 | Silux TM Plus* | 0 | 15 | 56 | 1.2 |
| | | | 4 | 24 | | |
| | | | 7 | 45 | | |
| | | | 14 | 65 | | |
| Example 1 | GFRP | Silux TM Plus | 0 | 14 | 28 | 0.04 |
| | | | 1 | 18 | | |
| | | | 4 | 23 | | |
| | | | 7 | 25 | | |

TABLE -continued

| Example or Comparative Example | Cartridge Material | Dental Composition | Aging Time (Days) | Extrusion Force (Kg) | Burst Strength (Kg) | 24 Hour Water Absorption (percent)[4] |
|---|---|---|---|---|---|---|
|  |  |  | 14 | 28 |  |  |
| Example 2 | GFRN | Silux ™ Plus | 0 | 15 | 50 | 0.14 |
|  |  |  | 4 | 14 |  |  |
|  |  |  | 12 | 15 |  |  |
| Comparative Example B | nylon-6 | Herculite ™ XR** | 0 | 25 | 56 | 1.0-11 |
|  |  |  | 2 | 35 |  |  |
|  |  |  | 3 | 37 |  |  |
|  |  |  | 6 | 38 |  |  |
|  |  |  | 9 | 45 |  |  |
|  |  |  | 15 | 55 |  |  |
| Example 3 | GFRP | Herculite ™ XR | 0 | 18 | 28 | 0.04 |
|  |  |  | 4 | 35 |  |  |
|  |  |  | 7 | 30 |  |  |
|  |  |  | 14 | 38 |  |  |
| Comparative Example C | nylon-6 | Prisma ™ APH*** | 0 | 16 | 56 | 1.0-11 |
|  |  |  | 3 | 35 |  |  |
|  |  |  | 6 | 45 |  |  |
|  |  |  | 9 | 52 |  |  |
|  |  |  | 15 | 58 |  |  |
| Example 4 | GFRP | Primsa ™ APH | 0 | 18 | 28 | 0.04 |
|  |  |  | 4 | 20 |  |  |
|  |  |  | 7 | 21 |  |  |
|  |  |  | 14 | 18 |  |  |

[4]Values taken from "Plastics Desk Top Data Bank", 6th Ed. International Plastics Selector, Inc., publisher.
*3M
**Kerr Manufacturing Company, a division of Sybron, Inc.
***L. D. Caulk Division of Dentsply International, Inc For each dental composition used, the corresponding data in the TABLE show that extrusion force increases less under accelerated aging conditions in a cartridge made of a material with a low 24 hour water absorption than in a cartridge of the same configuration made of nylon-6. The data in the TABLE also show that for each of the dental compositions used the increase in viscosity under accelerated aging conditions is minimized in a cartridge made of a material with a low 24 hour water absorption.

In order to minimize the likelihood that a cartridge will accidentally burst during use, the extrusion force should not exceed the cartridge's burst strength. EXAMPLE 2 shows that nylon-6,12 can be filled with a reinforcing filler in order to lower its 24 hour water absorption and thus obtain a cartridge that exhibits stable aging behavior and a burst strength substantially greater than its extrusion force.

We claim:

1. A cartridge specially adapted to be mounted in a hand-held ejector-type gun, comprising:
   a hollow cartridge body having an inner wall defining an elongate inner chamber open at one end of the body and adapted at the open end to be detachably mounted in the gun, and having at the opposite end of the body an orifice to allow discharge of a dental composition from the inner chamber; and
   a piston inserted into the open end of the body,
   wherein the body has a burst strength greater than that of an otherwise identical body made entirely of polypropylene, and the inner wall material has a 24 hour water absorption less than that of nylon-6.

2. A cartridge according to claim 1, wherein the inner wall material has a 24 hour water absorption less than about 1 percent.

3. A cartridge according to claim 1, wherein the inner wall material has a 24 hour water absorption less than or equal to about 0.5 percent.

4. A cartridge according to claim 1, wherein the inner wall material has a 24 hour water absorption less than or equal to about 0.3 percent.

5. A cartridge according to claim 1, wherein the inner wall material is a polymeric material.

6. A cartridge according to claim 1, with a burst strength of at least about 25 kg.

7. A cartridge according to claim 1, wherein the inner chamber contains a dental restorative composition comprising a polar monomer.

8. A cartridge according to claim 7, wherein the dental composition comprises diglycidylmethacrylate of Bisphenol A and triethyleneglycol dimethacrylate.

9. A cartridge according to claim 7, which, when filled with a dental composition and aged two weeks according to the Extrusion Force Test, has an extrusion force that does not exceed its burst strength.

10. A cartridge specially adapted to be mounted in a hand-held ejector-type gun, comprising:
    a hollow cartridge body having an inner wall defining an elongate inner chamber open at one end of the body and adapted at the open end to be detachably mounted in the gun, and having at the opposite end of the body an orifice to allow discharge of a dental composition from the inner chamber; and
    a piston inserted into the open end of the body,
    wherein the body has a burst strength greater than that of an otherwise identical body made entirely of polypropylene, and the inner wall material has a 24 hour water absorption less than that of nylon-6, and wherein the inner wall material comprises about 10 percent by weight to about 60 percent by weight reinforcing filler, and from about 40 percent by weight to about 90 percent by weight polymeric material, based on the total weight of the material.

11. A cartridge specially adapted to be mounted in a hand-held ejector-type gun, comprising:
    a hollow cartridge body having an inner wall defining an elongate inner chamber open at one end of the body and adapted at the open end to be detachably mounted in the gun, and having at the opposite end of the body an orifice to allow discharge of a dental composition from the inner chamber; and a piston inserted into the open end of the body, wherein the body has a burst strength greater than that of an otherwise identical body made entirely of polypropylene, and the inner wall material has a 24 hour water absorption less than that of nylon-6, and wherein the inner wall material comprises about 10 percent by weight to about 60 percent by weight reinforcing filler, and from about 40 percent by weight to about 90 percent by weight polymeric material, based on the total weight of the material, wherein the filler comprises glass.

12. A cartridge specially adapted to be mounted in a hand-held ejector-type gun, comprising:

a hollow cartridge body having an inner wall defining an elongate inner chamber open at one end of the body and adapted at the open end to be detachably mounted in the gun, and having at the opposite end of the body an orifice to allow discharge of a dental composition from the inner chamber; and a piston inserted into the open end of the body, wherein the body comprises 50 percent to about 70 percent by weight nylon-6,12, and about 30 percent to about 50 percent by weight reinforcing filler, based on the total weight of the material.

13. A cartridge specially adapted to be mounted in a hand-held ejector-type gun, comprising:

a hollow cartridge body having an inner wall defining an elongate inner chamber, open at one end of the body and adapted at the open end to be detachably mounted in the gun, and having at the opposite end of the body an orifice to allow discharge of a dental composition from the inner chamber; and a piston inserted into the open end of the body, wherein the cartridge has an extrusion force less than the extrusion force of an otherwise identical nylon-6 cartridge when both are filled with a dental composition and aged two weeks according to the Extrusion Force Test, and wherein the body has a burst strength greater than that of an otherwise identical body made entirely of polypropylene.

14. A cartridge according to claim 13, which has an extrusion force less than about 80 percent of the extrusion force of an otherwise identical nylon-6 cartridge when both are filled with a dental composition and aged two weeks according to the Extrusion Force Test.

15. A cartridge according to claim 13, wherein the body is made entirely of a polymeric material.

16. A cartridge according to claim 15, wherein the polymeric material has a tensile strength greater than that of polypropylene and a 24 hour water absorption less than that of nylon-6.

17. A cartridge according to claim 13, wherein the inner chamber contains a dental restorative composition comprising a polar monomer.

18. A cartridge according to claim 17, wherein the dental composition comprises diglycidylmethacrylate of Bisphenol A and triethyleneglycol dimethacrylate.

19. A cartridge specially adapted to be mounted in a hand-held ejector-type gun, comprising:

a hollow cartridge body having an inner wall defining an elongate inner chamber open at one end of the body and adapted at the open end to be detachably mounted in the gun, and having at the opposite end of the body an orifice to allow discharge of a dental composition from the inner chamber; and a piston inserted into the open end of the body, wherein the cartridge has an extrusion force less than the extrusion force of an otherwise identical nylon-6 cartridge when both are filled with a dental composition and aged two weeks according to the Extrusion Force Test, and wherein the body has a burst strength greater than that of an otherwise identical body made entirely of polypropylene, and wherein the body is made of material comprising about 10 percent by weight to about 60 percent by weight reinforcing filler, and from about 40 percent by weight to about 90 percent by weight polymeric material based on the total weight of the material.

20. A cartridge specially adapted to be mounted in a hand-held ejector-type gun, comprising:

a hollow cartridge body having an inner wall defining an elongate inner chamber, open at one end of the body and adapted at the open end to be detachably mounted in the gun, and having at the opposite end of the body an orifice to allow discharge of a dental composition from the inner chamber; and a piston inserted into the open end of the body, wherein the cartridge has an extrusion force less than the extrusion force of an otherwise identical nylon-6 cartridge when both are filled with a dental composition and aged two weeks according to the Extrusion Force Test, and wherein the body has a burst strength greater than that of an otherwise identical body made entirely of polypropylene, wherein the body is made of material comprising about 10 percent by weight to about 60 percent by weight reinforcing filler, and from about 40 percent by weight to about 90 percent by weight polymeric material based on the total weight of the material, and wherein the filler comprises glass.

21. A cartridge specially adapted to be mounted in a hand-held ejector-type gun, comprising:

a hollow cartridge body having an inner wall defining an elongate inner chamber, open at one end of the body and adapted at the open end to be detachably mounted in the gun, and having at the opposite end of the body an orifice to allow discharge of a dental composition from the inner chamber; and a piston inserted into the open end of the body, wherein the body is made of material comprising 50 percent to about 70 percent by weight nylon-6,12 and about 30 percent to about 50 percent by weight reinforcing filler, based on the total weight of the material.

22. A cartridge specially adapted to be mounted in a hand-held ejector-type gun, comprising:

a hollow cartridge body having an inner wall defining an elongate inner chamber, open at one end of the body and adapted at the open end to be detachably mounted in the gun, and having at the opposite end of the body an orifice to allow discharge of a dental composition from the inner chamber; and a piston inserted into the open end of the body, wherein the body is made of material comprising about 50 percent by weight nylon-6,12 and about 50 percent by weight glass.

* * * * *